106-85    AU 113    EX
4/13/82   OR  4,324,591

United States Patent [19]
Beede et al.

[11] 4,324,591
[45] Apr. 13, 1982

[54] MODIFYING AGENTS FOR ION-LEACHABLE CEMENT COMPOSITIONS

[75] Inventors: Charles H. Beede, East Brunswick; Richard N. Zirnite, Somerset, both of N.J.

[73] Assignee: Johnson & Johnson, New Brunswick, N.J.

[21] Appl. No.: 204,984

[22] Filed: Nov. 7, 1980

[51] Int. Cl.$^3$ .................................................. C09K 3/00
[52] U.S. Cl. ........................................ 106/85; 106/35; 128/87 R; 260/998.11; 524/432; 524/433; 524/430
[58] Field of Search ................... 106/35, 85, 90, 97; 260/29.6 S, 998.11; 128/87 R

[56] References Cited
U.S. PATENT DOCUMENTS
4,174,334  11/1979  Bertenshaw et al. .................. 106/35

*Primary Examiner*—James Poer
*Attorney, Agent, or Firm*—Jason Lipow

[57] ABSTRACT

A cementitious composition is provided which includes a dry ion-leachable glass powder and further includes an essentially water-insoluble non-hydroxylic polycarboxylic aromatic compound. The composition is usable in orthopedic bandages, and particularly those bandages which are activated by dipping the substrate carrying the compound into a water-containing vessel to activate the compound.

20 Claims, No Drawings

MODIFYING AGENTS FOR ION-LEACHABLE CEMENT COMPOSITIONS

BACKGROUND OF THE INVENTION

This invention relates to cement compositions comprising ion leachable inorganic compounds preferably in the form of glasses. In particular, this invention relates to providing additives, hereinafter modifying agents, for altering and controlling the reaction time associated with such cement compositions.

Ion leachable inorganic compounds such as the oxides of aluminum, zinc, magnesium, and calcium have been intermixed with other components such as silicone and formed into glasses which, when combined with such hydrogen donating compounds such as acids, will set up into a cementitious mass. The mechanisms for the reaction has been described by Alan D. Wilson, et al. (Journal of Dental Research, Volume 58, No. 3 at pps. 1065–1071, March 1979), and can be represented by the generic equation:

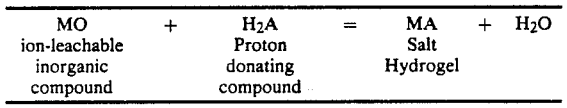

| MO | + | H$_2$A | = | MA | + | H$_2$O |
| ion-leachable inorganic compound | | Proton donating compound | | Salt Hydrogel | | |

Cements utilizing this mechanism have generally taken the form of glass powders incorporating the ion leachable inorganic. These are reacted with acid solutions such as aqueous, poly(carboxylic acid) solutions to form a salt hydrogel structure which sets up to a hard mass. Such cement forming compositions have been suggested for use in applications such as dental cements and for orthopedic purposes; i.e., casts and splints. For example, a fluoro alumino silicate glass powder has been suggested for use as the ion leachable component for dental cement as in British Pat. No. 1,316,129. Similarly, such a composition has been suggested for use in orthopedic surgery as in U.S. Pat. Nos. 4,143,018 and 4,043,327.

When using such compositions for orthopedic purposes, for example, certain criteria must be met. The composition, when rendered reactive, must be capable of providing sufficient "working time," i.e., sufficient time from the start of mixing the reactants to allow the doctor time to apply and mold the cast into shape before the material reaches a stage where it is no longer maleable. Generally, such times should be at least about 2 minutes and preferably from about 4 to about 6 minutes.

At the end of the working time, it is most desirable that the cast set to a rock-like state as quickly as possible. While most cements, even after obtaining a rock-like appearance, do not reach their ultimate strength for long periods of time, the material should reach sufficient compressive strength to allow a patient to leave the doctor's office i.e. should be sufficiently hard enough to preclude deformation under expected stresses. This period is referred to as the "setting time" and should be about 6 to about 15 minutes after the cast is applied.

Prior workers in the field have discovered that the rate of setting; i.e., the working and setting times, can be greatly affected by the addition of certain agents which have alternatively been referred to in the art as chelating agents, complexing agents, accelerating agents, or the like. (See for example, Wilson, et al., Journal of Dental Research, Volume 55 No. 3, Pages 489–495, 1976; Crisp, et al., Journal of Dental Research, Volume 55 No. 6, Pages 123–131, 1976; Crisp, et al., Journal of Dentistry, Volume 7, No. 4, Pages 304–319, 1979).

As has been described in the aforementioned U.S. Pat. No. 4,043,327 one way of varying the setting times of these compositions is to add to the mixture an inorganic dicarboxylic or hydrocarboxylic acid. It is stated that this addition appears to exert a chelating effect on calcium ions produced when water is added. Such acids are described in this patent as including tartaric, succinic, oxalic, citric, ascorbic, gluconic or adipic acids. In my co-pending patent application filed on this same day, I have disclosed the use of a particular form of tartaric acid; namely, tartaric acid including a major portion of the racemic mixture of the optically neutral d,l-isomer, which has particular advantage as an accelerating agent.

Unfortunately, it has now been discovered that there is one major drawback in providing compositions including such modifying or accelerating agents as those enumerated above. Specifically, when employing these compositions in the manner such as an orthopedist might, the compositions are generally in the dry form adhered to certain substrates such as gauze, for example. The practitioner prepares the composition for application by first dipping the entire bandage in a bucket or other container of water thereby beginning the gelation reaction. He then molds the cast onto the limb of the patient and allows it to set. The problem encountered with the aforementioned accelerating agents is that they are all, to a great degree, water soluble and if the practitioner follows his usual practice, the compositions are introduced into an environment which contains a large excess of water. Depending upon how long the composition resides in the bucket of water, more or less of the accelerating agent will be dissolved into the large excess of water and become unavailable for the gelation reaction, particularly after the bandage is removed from the water and placed onto the limb of the patient. This variation in solubilization of the modifying agent produces a concomitant variation in the performance of the product. Stated in other words, depending on the idiosyncrasies and methods of the practitioner, the setting and working times of a given composition will vary in an uncontrolled manner. Accordingly, there is a need for providing cementitious compositions with modifying agents which are not greatly affected by the variation in their use.

SUMMARY OF THE INVENTION

In accordance with this invention, it has been discovered that a dry mixture of ion leachable glass powder, poly(carboxylic acid), and a modifying agent may be provided in which the modifying agent is not substantially water soluble but instead is insoluble and will not be affected by the idiosyncrasies of the user in introducing the composition into a water medium. Specifically, it has been discovered that properties such as the setting time and the working time of such cementitious compositions may be modified by employing, as the modifying agent, essentially water insoluble, non-hydroxylic polycarboxylic aromatic compounds which have a water-solubility less than about 5.0 grams per 100 grams of water at room temperature. In a specific embodiment, the water insoluble poly carboxylic aromatic compounds are chosen to be that indicated in Formula 1 below:

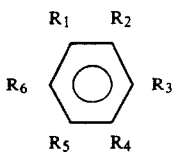
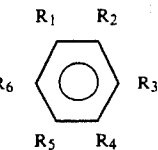

wherein $R_1$, $R_2$, $R_3$, $R_4$, $R_5$, and $R_6$ are selected from the group consisting of —H, —COOH, and —CH$_2$—COOH.

Preferably, such polycarboxylic aromatic compounds are employed in a ratio of about 0.01 grams per gram of ion-leachable glass to about 0.1 grams per gram and more preferably in a ratio of about 0.04 grams per gram to about 0.08 grams per gram.

DETAILED DESCRIPTION OF THE INVENTION

The powdery cementitious mixtures of this invention comprise ion leachable inorganic compounds, poly(carboxylic acid) and a modifying agent which, in accordance with the teachings of this invention, is chosen to be a water-insoluble non-hydroxylic polycarboxylic, aromatic compound.

The ion leachable inorganic compounds are preferably introduced in the form of glass powders which have been formed from the oxides of alkali, alkaline, aluminum and zinc metals along with silica. As has been more fully discussed in a commonly assigned pending U.S. Patent Application filed on this same day and incorporated herein by reference, it has advantages to provide such glass powder in as homogenous a state as is possible and with a controlled and precise degree of crystallinity. In this aforementioned U.S. patent application, a method for realizing these criteria is described and basically comprises feeding shaped charged materials into an electric furnace, melting the materials to a molten mixture, blowing the molten mixture into thin glass fibers, and immediately quenching the fibers in a water bath. The quenched fibers are then dried and milled into the desired glass powder form. The poly(carboxylic acid) may be one or more poly(acids) or their precursors and include polymers of monocarboxylic acids, monocarboxylic acid anhydrides, dicarboxylic acids and dicarboxylic acid anhydrides as well as interpolymers of the above or interpolymers of the above and other ethylenically unsaturated monomers. Examples of usable acids and precursors are poly(acrylic acid), itaconic acid, acrylic acid copolymers, itaconic acid polymer, poly(arylsulfonic acids), poly(methacrylic acid), ethyl acrylate-acrylic acid copolymer and the like. Also usable are a series of poly(methyl vinyl ether/maleic anhydride) copolymers sold by the GAF corporation under the trade name "Gantrez." All of these are available as finely divided solids which may be blended with the other ingredients.

In accordance with the teachings of this invention, the modifying agent is selected to comprise a water-soluble non-hydroxylic, polycarboxylic aromatic compound which is soluble in water to a degree less than about 1.0 grams to a gram of water. In a preferred embodiment such a compound has the formula of:

wherein $R_1$, $R_2$, $R_3$, $R_4$, $R_5$ and $R_6$ are selected from the group consisting of —H, —COOH, or —CH$_2$COOH. Exemplary compounds of this group include the bicarboxylic acids such as phthalic acid, isophthalic acid; the tri-carboxylic acids such as hemimellitic acid, trimecic acid and trimellitic acid; and the tetra-carboxylic acids such as pyromellitic acid.

It should be noted that it is not necessary that the carboxylic groups be directly bonded to a carbon atom within the benzene ring, provided however, that all other criteria described herein is complied with; i.e., that the compound be essentially water insoluble and non-hydroxylic. Accordingly, for example, compounds such as 1,4-phenylenediacetic acid are also quite effective in the compositions of this invention.

The solubilities of exemplary acids of the group above are illustrated in table I below:

TABLE 1

| Modifying Agent | Solubility @ 21° C. (gm/100 gm H$_2$O) |
| --- | --- |
| Phthalic acid | 0.54 |
| Isophthalic acid | 0.01 |
| Terephthalic acid | 0.001 |
| Pyromellitic acid | 1.23 |
| 1,4-phenylenediacetic acid | 0.008 |

As can be seen from the above Table, these acids are only very slightly soluble. Accordingly, when combined with the other ingredients and adhered to a substrate such as a gauze bandage, as is the practice in the orthopedic field, these bandages, when dipped in an excess of water, will lose only an insignificant amount of the modifying agent and, hence, the composition of the modifying agent remaining on the bandage will be substantially unchanged. Therefore, irrespective of the length of time or the degree of aggitation that the bandage is subjected to when in the water bath, the composition will remain essentially constant and perform its predetermined function as a modifying agent. In this connection, it should be noted that the modifying agent allows the formulator to control the working and setting times and, in some instances, to increase the compressive strength of the resulting cementitious composition. While the quantity of modifying agent to be used in a given composition will vary with such factors such as the desired working time, the desired setting time, the desired strength, and also the composition of the remaining ingredients, generally a range of from about 0.03 grams of modifying agent per gram of ion-leachable inorganic compound to about 0.1 grams per gram is suitable. Still more preferably, the range should be generally from about 0.04 grams per gram to about 0.08 grams per gram.

The invention is further illustrated by consideration of the following examples:

EXAMPLE 1

A series of samples are prepared consisting of a powdery mixture of ground ion-leachable glass, polyacrylic acid, and various modifying agents of the kind described herein. The powdered glass ingredient is made by procedures described in the above-referred to, commonly assigned, U.S. patent application filed on this day by Smyth and employs the following formulation: 4 molar parts $SiO_2$, 2.5 molar parts $Al_2O_3$, and 3.5 molar parts CaO. The proportions of the ingredients, the characteristics of the polyacrylic acid, and the type of modifying agent are all as listed below in Table II. The dry components, i.e., the glass, the polyacid, and the various modifying agents are combined in various combinations and proportions to form the substantially homogeneous powder compositions defined in Table II below. The powdered compositions are mixed with water, in the proportions shown in the Table, to form a moldable paste. The paste is then quickly packed into a 0.635 centimeter diameter by 1.27 centimeter long bore bored through the center of a 1.27 centimeter thick circular Teflon mold. The filled molds are placed between glass plates weighted down by a 200 gram weight and allowed to cure for 72 hours at 70° F. (21° C.) to form cylindrical pellets. The pellets are then removed from the mold and tested in an Instron Tester operating at a head speed of 0.05 centimeter per minute to determine the compressive strength which is reported in Table II below in pounds per square inch.

EXAMPLE 2

A series of slurries, having a 65% solids content was prepared by dispersing the powderous compositions defined in Table III below in a one-to-one (by weight) solution of methanol and methoxyethanol. The slurries are coated onto 32×28 count gauze, laid against silicone releasing paper, by using the 20 milimeter gap of a Gardner multiple clearance applicator. The resulting casting tape is air dried for 1.75 hours and then heated in a steam cabinet for one hour. The coating weight of the dry tape is 13.8 ounces/yd$^2$. A 40"×1.5" strip of the casting tape described above is dipped into a pail of water at 30° C. for 20 seconds, lightly squeezed and the excess water shaken off. The tape is then wrapped around a wax paper covered U-shaped block of wood such that there are five plies of bandages across the space between the legs of the U. An English #4 sharp needle is placed in a holder such that the total weight of the needle and the holder is 300 grams. The needle is rested on the surface of the bandage over the space between the legs of the U-shaped block at intervals of 15 seconds. Initially, the weight of the needle and the holder is sufficient to push the needle through the bandage. After a period of time, hereinafter referred to as the needle test set time, the bandage can no longer be

TABLE II

| | Cement Composition (Powder) | | | | | | Water Addition | Curing Time | Compressive |
|---|---|---|---|---|---|---|---|---|---|
| | Glass | Poly(Acrylic Acid) | | | Modifying Agents | | (ml H$_2$O/gm | Days | Strength |
| Sample | Parts | Mole. Wt. | Eqiuv. Wt. | Parts | Type | Parts | powder) | 70° C. | (PSI) |
| 1 | 100 | 125,000 | 79.2 | 12 | d-Tartaric | 6 | 0.25 | 3 | 3587 |
| 2 | 100 | 125,000 | 79.2 | 12 | d,l-Tartaric | 6 | 0.25 | 3 | 6370 |
| 3 | 100 | 125,000 | 79.2 | 12 | Terephthalic | 6 | 0.25 | 3 | 6440 |
| 4 | 100 | 249,000 | 84.3 | 12 | Phthalic | 6.3 | 0.25 | 6 | 4071 |
| 5 | 100 | 249,000 | 84.5 | 12 | Isophthalic | 6.3 | 0.25 | 6 | 5177 |
| 6 | 100 | 249,000 | 84.5 | 12 | 1,4-Phenylene-diacetic | 7.4 | 0.25 | 6 | 5199 |
| 7 | 100 | 249,000 | 84.5 | 12 | Pyromellitic | 9.6 | 0.25 | 6 | 6281 |
| 8 | 100 | 164,700 | 81.3 | 33.3 | d,l-Tartaric | 10.0 | 0.20 | 3 | 13130 |
| 9 | 100 | 164,700 | 81.3 | 33.3 | Terephthalic | 10.0 | 0.20 | 3 | 7766 |
| 10 | 100 | 164,700 | 81.3 | 33.3 | 1,4-Phenyl-diacetic | 10.0 | 0.20 | 3 | 7959 |
| 11 | 100 | 164,700 | 81.3 | 33.3 | Isophthalic | 10.0 | 0.20 | 3 | 8222 |
| 12 | 100 | 164,700 | 81.3 | 33.3 | Phthalic | 10.0 | 0.20 | 3 | 8856 |
| 13 | 100 | 164,700 | 81.3 | 33.3 | Pyromellitic | 10.0 | 0.20 | 3 | 12139 |

As can be seen from Table II, the use of the modifying agents of this invention in no way is disadvantageous as compared to the use of the prior art agent of sample 1, namely, d-tartaric acid. In fact, in most cases, an increase in compressive strength is noted. Further, little is lost when using the modifying agents of this invention as compared to the use of the d,l-tartaric acid agent described in our co-pending application. As has been described herein, the use of the agents described in this invention have the added advantage of not being water-soluble and, hence, performing uniformly irrespective of the method by which the applicator adds water to the cementitious composition.

punctured by the mere weight of the needle and holder. These times are recorded below as the Needle Set Time. Additionally, three strips measuring 1.5 inches by 12 inches, of the casting tape described above, are dipped into a pail of water at 30° C. for 20 seconds. Each tape is then immediately wrapped around a 0.5 inch diameter steel rod covered with wax paper. The plies are smoothed as the wrapping progresses in a manner very similar to the technique used in wrapping plaster casting tapes. The casts are cured at 70° F. (21° C.) for 3 days. The deflection strength is then measured by using an Instron Tester to determine the average value for the force required to deflect the hollow cylinder by reducing the inside diameter by 15%. This value is recorded as the deflection strength.

TABLE III

| | Cement Composition (Powder) | | | | | Needle Test | Deflect. |
|---|---|---|---|---|---|---|---|
| | Glass | Poly (Acrylic Acid) | | Modifying Agents | | Set Times | Strength |
| Sample | Parts | Mole. Wt. | Parts | Type | Parts | (Min:Sec.) | (lb/gm) |
| 14 | 54 | 112,400 | 27.0 | — | — | 34:00 | — |
| 15 | 54 | 112,400 | 22.7 | Phthalic | 4.3 | 12:55 | 20.2 |
| 16 | 54 | 112,400 | 22.7 | Isophthalic | 4.3 | 14:40 | 19.0 |

TABLE III-continued

| Sample | Cement Composition (Powder) | | | | | Needle Test Set Times (Min:Sec.) | Deflect. Strength (lb/gm) |
|---|---|---|---|---|---|---|---|
| | Glass Parts | Poly (Acrylic Acid) Mole. Wt. | Parts | Modifying Agents Type | Parts | | |
| 17 | 54 | 112,400 | 22.7 | Terephthalic | 4.3 | 9:00 | 21.8 |
| 18 | 54 | 112,400 | 22.7 | Pyromellitic | 4.3 | 10:48 | 19.5 |
| 19 | 54 | 112,400 | 22.7 | 1,4-Phenylene-diacetic | 4.3 | 11:07 | 22.9 |
| Coating Solvent: 27 Parts Menthanol/27 Parts Ethoxyethanol | | | | | | | |
| 20 | 60 | 76,400 | 20.0 | — | — | 13:57 | 20.2 |
| 21 | 60 | 76,400 | 16.8 | 76,400 | 3.2 | 7:16 | 17.5 |
| 22 | 60 | 76,400 | 16.8 | Isophthalic | 3.2 | 12:39 | 19.9 |
| 23 | 60 | 76,400 | 16.8 | Terephthalic | 3.2 | 11:34 | 18.6 |
| 24 | 60 | 76,400 | 16.8 | Pyromellitic | 3.2 | 7:53 | 18.9 |
| 25 | 60 | 76,400 | 16.8 | 1,4-Phenylene-diacetic | 3.2 | 10:23 | 19.1 |
| Coating Solvent: 21.5 Parts Methanol/21.5 Parts Methoxyethanol | | | | | | | |
| 26 | 64 | 112,400 | 16.0 | — | — | 10:12 | 17.0 |
| 27 | 64 | 112,400 | 13.4 | Phthalic | 2.6 | 7:58 | 7.7 |
| 28 | 64 | 112,400 | 13.4 | Isophthalic | 2.6 | 11:07 | 17.0 |
| 29 | 64 | 112,400 | 13.4 | Terephthalic | 2.6 | 5:57 | 14.2 |
| 30 | 64 | 112,400 | 13.4 | Pyromellitic | 2.6 | 5:03 | 11.1 |
| 31 | 64 | 112,400 | 13.4 | 1,4-Phenylene-diacetic | 2.6 | 9:52 | 15.6 |
| Coating Solvent: 21.5 Parts Methanol/21.5 Parts Methoxyethanol | | | | | | | |

As can be seen from the above Table, by using the modifying agents of this invention, there is a substantial improvement in the needle set times reducing the time for casts to set by a considerable margin. Similarly, in almost each instance, there is an improvement in the deflection strength of the cast.

What is claimed is:

1. In a cementitious composition comprising dry, ion-leachable glass powder, the improvement wherein said composition further comprises an essentially water insoluble, non-hydroxylic polycaroxylic aromatic compound having a solubility of less than 5 grams per 100 grams of water at room temperature.

2. The composition of claim 1 wherein the polycarboxylic aromatic compound is a polycarboxylic aromatic compound having the formula:

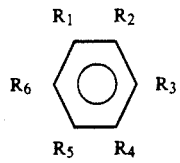

wherein $R_1$, $R_2$, $R_3$, $R_4$, $R_5$, and $R_6$ are selected from the group consisting of —H, —COOH, and —CH$_2$COOH.

3. The composition of claim 2 wherein said polycarboxylic aromatic compound is a bicarboxylic aromatic acid.

4. The composition of claim 3 wherein said bicarboxylic aromatic acid is phthalic acid.

5. The composition of claim 4 wherein said bicarboxylic aromatic acid is isophthalic acid.

6. The composition of claim 2 wherein said polycarboxylic aromatic compound is a tri-carboxylic aromatic acid.

7. The composition of claim 6 wherein said tri-carboxylic aromatic acid is hemiomellatic acid.

8. The composition of claim 6 wherein said tri-carboxylic aromatic acid is trimecic acid.

9. The composition of claim 6 wherein said tri-carboxylic aromatic acid is trimellitic acid.

10. The composition of claim 2 wherein said polycarboxylic aromatic compound is a tetra-carboxylic acid.

11. The composition of claim 10 wherein said tetra-carboxylic acid is pyromellitic acid.

12. The composition of claim 2 wherein said polycarboxylic aromatic compound is 1,4-phenylene diacetic acid.

13. The composition of claim 1 wherein said polycarboxylic aromatic compound is present in the ratio of about 0.01 grams to about 0.1 per gram of ion-leachable glass.

14. The composition of claim 2 wherein said polycarboxylic aromatic compound is present in the ratio of about 0.07 to about 0.09 grams per gram of ion-leachable glass.

15. The composition of claim 1 further comprising a proton donating compound.

16. The composition of claim 15 wherein said proton donating compound is a poly(carboxylic acid).

17. The composition of claim 16 wherein said poly(carboxylic acid) is poly(arylic acid).

18. The composition of claim 1 wherein said glass powder is formed from molten inorganic compounds selected from the oxides of alkali, alkaline earth, aluminum and zinc metals and mixtures of these in combination with quartz.

19. The composition of claim 1 in a dental cement.

20. The composition of claim 1 adhered to a bandage substrate.

* * * * *